Figure 1:
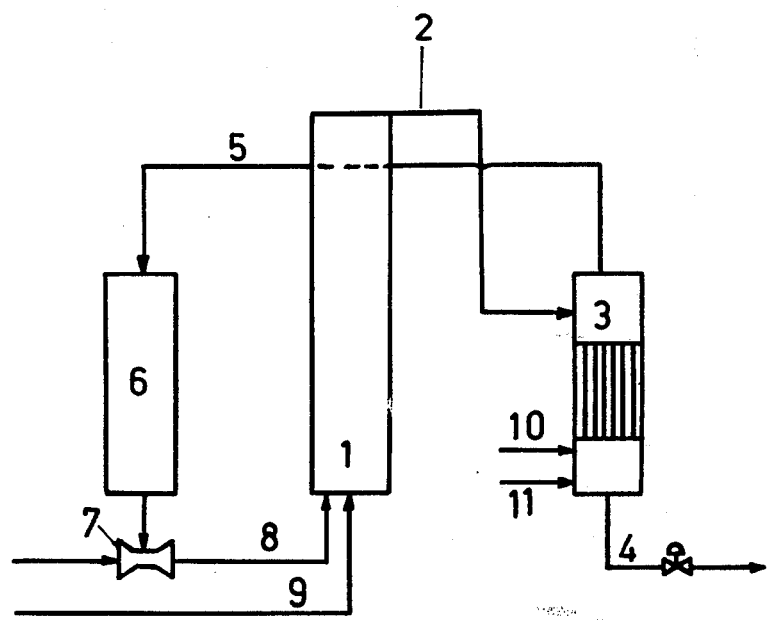

United States Patent

Guadalupi et al.

[11] 3,954,861
[45] May 4, 1976

[54] PROCESS FOR PRODUCING UREA

[75] Inventors: Mario Guadalupi, Milan; Umberto Zardi, San Donato Milanese, both of Italy

[73] Assignee: Snamprogetti S.p.A, San Donato Milanese, Italy

[22] Filed: Oct. 11, 1974

[21] Appl. No.: 514,237

Related U.S. Application Data

[63] Continuation-in-part of Ser. No. 795,892, Feb. 3, 1969, abandoned.

[30] Foreign Application Priority Data

Feb. 5, 1968 Italy .................. 12409/68

[52] U.S. Cl............................................... 260/555 A
[51] Int. Cl.² ........................................ C07C 126/00
[58] Field of Search .............................. 260/555 A

[56] References Cited
UNITED STATES PATENTS

| | | | |
|---|---|---|---|
| 3,038,285 | 6/1962 | Mavrovic | 260/555 |
| 3,270,051 | 8/1966 | Braun | 260/555 |
| 3,357,901 | 12/1907 | Otsuka et al. | 260/555 |
| 3,378,585 | 4/1968 | Fauser | 260/555 |
| 3,406,201 | 10/1968 | Baumann et al. | 260/555 |
| 3,436,317 | 4/1969 | Otsuka | 260/555 |
| 3,530,180 | 9/1970 | Giommi | 260/555 |
| 3,607,938 | 9/1971 | Braun | 260/555 |

FOREIGN PATENTS OR APPLICATIONS

| | | | |
|---|---|---|---|
| 1,285,786 | 1/1962 | France | 260/555 |
| 1,188,051 | 4/1970 | United Kingdom | 260/555 |

*Primary Examiner*—Oscar R. Vertiz
*Assistant Examiner*—Eugene T. Wheelock
*Attorney, Agent, or Firm*—Ralph M. Watson

[57] ABSTRACT

In a process for the production of urea from ammonia and carbon dioxide by feeding ammonia and carbon dioxide into a reactor, reacting the ammonia and carbon dioxide so as to produce an effluent aqueous solution of urea contaminated with ammonium carbamate, stripping the ammonium carbamate from the said solution in the presence of a stripping agent selected from ammonia and carbondioxide so as to produce an aqueous solution of urea substantially free from ammonium carbamate and a vapor phase of ammonia and carbon dioxide, and condensing ammonia and carbon dioxide to form a solution of carbamate for recycle into the reactor, and feeding ammonium carbamate to the reactor by entraining it in a stream of ammonia fed to the reactor through an ejector.

5 Claims, 1 Drawing Figure

2

PROCESS FOR PRODUCING UREA

CROSS REFERENCE TO RELATED APPLICATION

This application is a continuation-in-part of our pending application, Ser. No. 795,892, now abandoned, filed Feb. 3, 1969.

This invention relates to a process for producing urea from carbon dioxide and ammonia and is particularly concerned with the recycling ammonium carbamate to the synthesis reactor.

Processes for producing urea are known, in which the splitting of ammonium carbamate contained in the reaction products flowing out of a reactor may be effected at a high pressure, even up to synthesis pressure. This splitting is effected with a stripping agent which, depending on the circumstances, may be ammonia (see British Pat. No. 1,031,528 and Oil and Gas International, July 1967, page 39); or carbon dioxide (see U.S. Pat. No. 3,356,723 and Nitrogen, No. 38, November, 1965).

These processes possess several advantages compared with conventional processes (see U.S. Pat. No. 2,848,493). As a matter of fact, the possibility of using gravity to recycle to the reactor the carbamate contained in the effluent stream from the synthesis zone using a single isobaric system for the reaction, the splitting and the condensation of the carbamate, represented a remarkable improvement compared with the conventional processes involving expensive pumping means for recycling the carbamate (see U.S. Pat. Nos. 3,356,723 and 3,530,180). However, when using gravity to effect the carbamate recycle, these processes require particular arrangements for the different parts of the synthesis apparatus, namely the synthesis reactor, carbamate decomposer and carbamate condenser.

The carbamate condenser must be disposed at a great height in order to have the water head necessary for compensating the load losses of the system and to be able to obtain the necessary recycle of the carbamate solution. This is very expensive for large plants since they require very heavy equipment and large diameter pipes. Thus, the installation of the carbamate condenser at a great height becomes very expensive, in fact, too expensive to be practicably feasible. Also, these processes introduce the problem of controlling and regulating the circulation of the carbamate to be recycled which in conventional processes may be carried out easily by pumping systems.

It is an object of the present invention to provide a process which avoids these drawbacks.

According to the present invention, there is provided a process for the production of urea, which comprises feeding ammonia and carbon dioxide into a reactor, reacting the ammonia and carbon dioxide so as to produce an effluent aqueous solution of urea contaminated with ammonium carbamate, stripping the latter from the said aqueous solution in the presence of a stripping agent selected from ammonia and carbon dioxide, so as to produce an aqueous solution of urea substantially free from ammonium carbamate condensing the ammonia and carbon dioxide to produce ammonium carbamate and recycling ammonium carbamate to the reactor by entraining condensed ammonium carbamate in ammonia which is fed to the reactor, thus utilizing energy present in the ammonia feed to supply the motive force for the carbamate recycle, and without need for a either a high water head or a recycle pump. The process of the present invention thus provides carbamate circulation irrespective of the position of the condenser in relation to the reactor and allows an easy control of the carbamate circulation.

The stripping is usually carried out in a single stage at a high pressure, preferably from 80 to 200 kg/cm.$^2$, and usually at a temperature of from 160° to 250°C.

Although the stripper may be in any position with respect to the reactor, it is of course convenient to position these units so that the effluent aqueous solution falls under a gravitational force from the reactor to the stripper.

Another advantage of the present invention is that the entraining provides a thorough mixing of the carbamate with the carbon dioxide or ammonia because of the high speed with which the ammonia is pushed into the entraining device.

Another economic and technological advantage arises from the fact that this mixing which has hitherto been carried out in the first part of the reactor, namely in the part nearest the reactants' inlet, thereby occupying an appreciable space of the reactor itself, may now, according to the present invention, be effected outside the reactor, and thus it is possible to make the reactor smaller.

Yet another advantage consists in the elimination of expensive equipment, for instance the pumps used for recycling the carbamate.

This is of importance, not only in savings in installation costs, since the cost of an ejector is only of the order of about 10% of the cost of the pumps conventionally used for carbamate recycling, but also in maintenance costs:

It is known that carbamate solution are highly corrosive and that this corrosive effect increases with increases in temperature and pressure. It is also known that the corrosivity of carbamate solution increases remarkably with increases in the rate of fluid flow. As carbamate solution recovered from a condenser normally has high crystallization temperature, many abrasive crystals may be present in the solution so that the erosion effected thereby adds to the corrosivity of the carbamate solution.

We have surprisingly found that it is possible to send to an urea reactor, without the usual phenomena of corrosion and abrasion, carbamate solutions at high pressure, temperature and flow rate.

These surprising results are obtained because, in our use of ammonia as motive fluid at high pressure, mixed with the carbamate solution, it not only prevents corrosion but also remarkably lowers the crystallization temperature of the ammonium carbamate, thus avoiding the presence of possible crystals which give rise to erosion phenomena.

Another surprising effect resides in the remarkable decrease in the reaction volume which is required when use is made of an ejector for pumping recycle carbamate to a reactor through the use of ammonia as the motive fluid.

The ejector produces a very effective mixing of the reagents, thus lowering the residence times in the reactor.

EXPERIMENTAL RESULTS

The foregoing observations are supported by the following experimental results:

1. Corrosivity of carbamate solution

A carbamate solution of the type conventionally recovered from a condenser was flowed through a stainless steel AISI 316 L pipe having 2 inch diameter under the following conditions:

| | |
|---|---|
| composition | $NH_3$ 35%, $CO_2$ 30%, water 35% |
| temperature | 170°C |
| pressure | 30 kg/cm$^2$ |
| fluid rate | 2 m/sec |
| corrosion rate | we observed a decreasing of the pipe thickness equal to 0.025 mm/year |

The test was repeated under the same conditions except that the pressure was brought to 160 kg/cm$^2$. The corrosion rate increased up to 0.3 mm/year. The abovesaid test (pressure = 160 kg/cm$^2$) was repeated by increasing the rate from 2 to 10 m/sec. The corrosion rate increased to 1 mm/year.

2. Employment of ammonia as motive fluid

The test described in the foregoing experiment No. 1 at a pressure of 160 kg/cm$^2$, was repeated by feeding the carbamate solution through the use of pure ammonia so that the content of ammonia in the solution brought up to 70%.

At a flow rate of the solution passing through the tube equal to 20 m/sec, the corrosion rate was lower than 0.01 mm/year.

3. Employment of other motive fluids

The test of experiment No. 1 at 160 kg/cm$^2$, was repeated by feeding the carbamate solution through the use of an inert gas (high purity nitrogen).

At a flow rate of the solution passing through the tube equal to 10 mm/sec the corrosion rate was 1.2 mm/year. (The thickness deductions were determined by a weighing).

For a better understanding of the present invention and to show how the same may be carried into effect, reference will now be made, by way of example, to the accompanying drawing which is a diagrammatic representation of an apparatus suitable for carying out the process of the present invention.

In the drawing there is shown a urea synthesis reactor 1, from the top of which the reaction products are led off by a pipe 2 to the upper portion of a carbamate stripper 3.

In the stripper 3, carbamate splitting is effected in presence of a gaseous countercurrent stream of $NH_3$ or $CO_2$ and the carbamate-free urea solution is discharged continuously from the bottom portion of the stripper 3 through a pipe 4. Ammonia and carbon dioxide vapours resulting from the carbamate splitting, together with vapourised carbamate, pass from the top of the stripper 3 through a pipe 5 to a carbamate condenser 6.

Carbamate solution coming from the condenser 6 is recycled to the reactor 1 by an entraining nozzle or ejector 7 disposed on reactant inlet pipe 8 which conveys ammonia feed the reactor 1. The other reactant, carbon dioxide, enters the reactor 1 by a further inlet pipe 9.

To carry out the carbamate stripping, depending on the circumstances, either carbon dioxide is admitted to the decomposer 3 through a pipe 10 or ammonia through a pipe 11.

What we claim is:

1. In a process for the production of urea from ammonia and carbon dioxide by feeding ammonia and carbon dioxide into a reactor, reacting the ammonia and carbon dioxide so as to produce an effluent aqueous solution of urea contaminated with ammonium carbamate, stripping the ammonium carbamate from the said solution in the presence of a stripping agent selected from ammonia and carbon dioxide so as to produce an aqueous solution of urea substantially free from ammonium carbamate and a vapour phase of ammonia and carbon dioxide, and condensing ammonia and carbon dioxide to form a solution of carbamate for recycle into said reactor, the improvement which consists in recycling said ammonium carbamate to the reactor by entraining the same in a stream of ammonia fed to said reactor through an ejector.

2. Process according to claim 1, wherein the stripping is effected in a single stage.

3. Process according to claim 1, wherein the stripping is effected at a temperature of from 160° to 250°C.

4. Process according to claim 1, wherein the stripping is effected at a pressure of from 80 to 200 kg/cm$^2$.

5. Process according to claim 1, wherein the effluent aqueous solution moves under a gravitational force from the reactor to the stripper.

* * * * *